United States Patent [19]

Cathignol et al.

[11] Patent Number: 5,219,401
[45] Date of Patent: Jun. 15, 1993

[54] APPARATUS FOR SELECTIVE DESTRUCTION OF CELLS BY IMPLOSION OF GAS BUBBLES

[75] Inventors: Dominique Cathignol, Genas; Jean-Yves Chapelon, Villeurbanne, both of France

[73] Assignees: Technomed Int'l; Institut National de la Sante, both of Paris, France

[21] Appl. No.: 481,896

[22] Filed: Feb. 20, 1990

[30] Foreign Application Priority Data

Feb. 21, 1989 [FR] France ................. 89 02250

[51] Int. Cl.$^5$ .................. A61M 31/00; A61B 17/00
[52] U.S. Cl. .................. 128/660.03; 128/24 AA
[58] Field of Search ........ 128/24 AA, 24 EZ, 660.03; 73/19.03

[56]  References Cited

U.S. PATENT DOCUMENTS

| | | | |
|---|---|---|---|
| 2,559,227 | 7/1951 | Rieber | 128/24 A |
| 4,265,251 | 5/1981 | Tickner | 128/660.02 |
| 4,316,391 | 2/1982 | Tickner | 73/861.25 |
| 4,689,986 | 9/1987 | Carson et al. | 73/19.03 |
| 5,040,537 | 8/1991 | Katakura | 128/24 AA |

FOREIGN PATENT DOCUMENTS

| | | |
|---|---|---|
| 072330 | 2/1983 | European Pat. Off. . |
| 123235 | 4/1983 | European Pat. Off. . |
| 148653 | 7/1985 | European Pat. Off. . |
| 206332 | 12/1986 | European Pat. Off. . |
| 273140 | 7/1988 | European Pat. Off. . |
| 320433 | 6/1989 | European Pat. Off. . |
| 2351247 | 4/1975 | Fed. Rep. of Germany . |
| 2538260 | 3/1977 | Fed. Rep. of Germany . |
| 2946662 | 5/1981 | Fed. Rep. of Germany . |
| 3517934 | 11/1986 | Fed. Rep. of Germany . |
| 1185226 | 10/1985 | U.S.S.R. .............. 73/19.03 |
| 8002365 | 11/1980 | World Int. Prop. O. . |
| 8703468 | 6/1987 | World Int. Prop. O. . |

OTHER PUBLICATIONS

Cokman et al., *Progress in Medical Ultrasound*, vol. 2, 1981, "Applications of Therapeutic Ultrasound in Opthalmology", pp. 263-270.

Anthony Donn, M. D., Ultrasonic Wave Liquefaction Of Vitreous Humor In Living Rabbits, Public Catalog A.M.A. Archives of Ophthalmology. Chicago: American Medical Association 20 v.:27 cm. Monthly, vol. 53, Date 1955.

Tickner et al., "Non-invasive Assessment of Pulmonary Hypertension Using Bubble UTS Resonance Pressure (BURP) Method", Nat. Tech. Inf. Service Report No. HR-62917-1A, Apr. 1977.

Kandler et al., :"State of the Art of Extracorporeal Shockwave Lithotripsy", 1987, Futura Publishing Co., pp. 111-145 and 97-110.

*Primary Examiner*—Ruth S. Smith
*Assistant Examiner*—Krista M. Pfaffle
*Attorney, Agent, or Firm*—Cohen, Pontani, Lieberman, Pavane

[57] ABSTRACT

The invention relates to an apparatus for selective destruction of cells including soft tissues and bones inside a living subject's body.

This apparatus is characterized in that it comproses:
  means for generating gas bubbles in situ within the cells to be selectively destroyed, and
  implosion means capable of provoking the implosion in situ of the gas bubbles, thereby destroying the cells to be destroyed which are adjacent the imploded gas bubbles.

The invention makes it possible to destroy cells inside a living subject's body by a non-invasive and extracorporeal and also extremely simple and efficient way, further permitting the treatment of metastases.

49 Claims, 1 Drawing Sheet

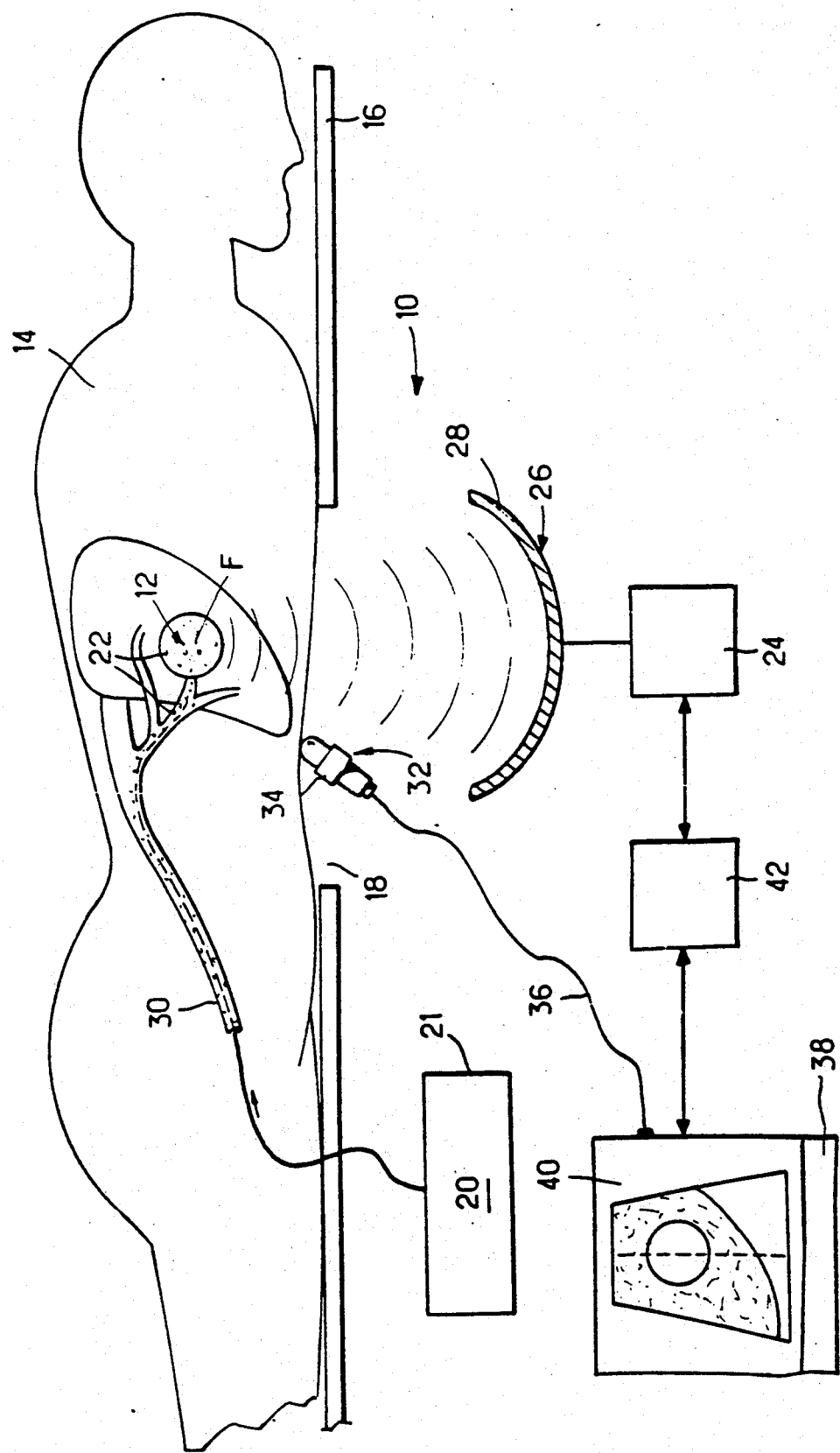

APPARATUS FOR SELECTIVE DESTRUCTION OF CELLS BY IMPLOSION OF GAS BUBBLES

FIELD OF THE INVENTION

The present invention relates essentially to an apparatus for selective destruction of cells including soft tissues and bones inside a living subject's body, particularly a mammal, including a human being.

BACKGROUND OF THE INVENTION

The prior art already describes various devices and methods for selectively destroying cells inside a living subject's body, in particular a mammal, including a human being. For example, U.S. Pat. No. 2,559,227 to RIEBER describes a shockwave-generating device for destroying cells inside a human body, using a truncated ellipsoid hermetically sealed by a membrane. The power needed for destroying the cells with this apparatus is relatively high, which is undesirable because of the existing risk of destroying sound cells.

Various other diagnosis methods have also been used for many years, for carrying out a non-invasive detection of pulmonary hypertension or the presence of tumors. TICKNER et al. for example, in their article "Non-invasive Assessment of Pulmonary Hypertension using Bubble UTS Resonance Pressure (BURP) Method", Nat. Tech. Inf. Service Rept. No. HR-62917-1A, April 1977, and also U.S. Pat. No. 4,265,251, have described a diagnosis method using the injection, in the blood vessels, of gas bubbles or of gas bubble precursor, in order to determine the blood pressure with the help of an ultrasonic apparatus, and the blood flow and to deduce therefrom the information which will reveal the presence or absence of heart or pulmonary disorders. U.S. Pat. No. 4,316,391 describes the use of a bubbles-precursor solid material in microcapsules encapsulating a gas of selected composition, the microcapsules having a diameter ranging between 0.5 and 300 μm. Document EP-A-0 072 330 describes improvements in the ultrasonic detection system using ultrasonic frequencies for generating fine bubbles in situ which bubbles are thereafter detected by monitoring the Doppler effect. Patents DE-A-29 46 662 and EP-A-0 273 140 describe the same teaching.

Document WO-A-80/02365 to RAZOR likewise uses the injection of microbubbles of gas having diameters in the 0.5 to 300 μm range, for detecting tumors as well as for delivering gaseous therapeutic agents selectively to tumors, as indicated in page 4, lines 4 to 9 and 14 to 30, and also in the claims.

It is clear from the foregoing that the prior art uses the gas bubbles essentially, if not solely, for diagnosis purposes, and in particular for measuring blood pressure. Only in document WO-A-80/02365 is there a possibility of selectively feeding gaseous therapeutic agents to tumors for treating them. This last solution is, on the other hand, hardly usable since the number of therapeutic agents which can be delivered in gaseous form and which are also capable of treating a given tumor, is extremely reduced so that this method of treating tumors by a gaseous therapeutic agent has not found an outlet in therapeutic practice.

SUMMARY OF THE INVENTION

It is the object of the present invention to provide a solution to the new technical problem consisting in finding a way of using gas bubbles for selective destruction of cells in situ, cells, including soft tissues and bones.

A further object of the invention is to solve this new technical problem by providing a solution permitting such selective destruction of cells mainly or essentially by the intervention of physical or mechanical phenomena, rather than by the action of active therapeutic products which requires long treatment periods and repeated administrations.

Yet another object of the present invention is to solve this new technical problem by providing a solution, permitting the selective destruction of cells in a living subject's body, particularly a mammal, including a human being, by using physical and mechanical effects combined with the introduction in situ of gas bubbles in the cells to be selectively destroyed, but requiring if possible only one treatment, or only an extremely reduced number of treatments, in non-invasive, essentially extracorporeal manner.

And finally another object of the present invention is to solve this new technical problem in an especially simplified, easy to reproduce, and extremely accurate way, namely a way offering very wide selectivity and usable on an industrial scale.

The present invention has, for the first time, solved the aforesaid technical problems in the way indicated hereinabove, which represents a decisive technical improvement, completely unexpected for anyone skilled in the art, and which makes it possible to treat a considerable number of complaints caused by malignant cells, such as, for example and non-restrictively, neoplasms of the liver, of the pancreas, of the kidney, of the testicles, of the ovary, of the womb, of the thyroid gland, of the parathyroid gland, of the breast, of the bile ducts, of the skin, of the sorrenace, of the muscle, of the prostate gland, of the salivary glands, of the urinary system, or of the bones.

Accordingly, a first aspect of the present invention is to provide an apparatus for the selective destruction of cells inside a living subject's body, particularly a mammal, including a human body, which is characterized in that it comprises:

means for generating gas bubbles in situ within the cells to be selectively destroyed, and implosion means capable of provoking the implosion in situ of the gas bubbles, thereby destroying the cells adjacent the imploded gas bubbles.

According to one advantageous embodiment of the apparatus according to the invention, said implosion means comprises means for generating high power acoustic waves. The acoustic waves are causing a positive pressure on the bubbles which compresses them until they disintegrate.

According to one particularly advantageous embodiment of the invention, said acoustic waves have a pressure wave ranging between several tens and several hundreds bars.

According to another particularly advantageous embodiment of the invention, said acoustic wave generating means comprise an acoustic generator of piezoelectric transducer type, preferably comprising means for focussing acoustic waves in a target-focus.

According to yet another advantageous embodiment of the invention, said acoustic wave generating means comprise a mechanical shockwave generator, preferably equipped with means of focussing mechanical shockwaves in a target-focus. Such mechanical shockwave generating apparatus comprise electrohydraulic generators, magnetostrictive type genetators, laser generators, explosive type generators.

According to one advantageous embodiment of the apparatus according to the invention, said gas bubble generating means comprise means for feeding the gas bubbles in situ.

According to a variant embodiment, the means for feeding the gas bubbles in situ comprise an injectable solution containing gas bubbles.

According to another variant embodiment of the invention, the gas bubble generating means contain a material which is a gas bubble precursor. In a variant embodiment, this material precursor of gas bubbles comprises capsules encapsulating the gas bubbles, said capsules being produced from a material which dissolves progressively in the blood stream. Such materials are described hereinafter.

According to another advantageous embodiment of the apparatus according to the invention, said gas bubble generating means comprise cavitation means generating gas bubbles in situ.

According to yet another advantageous embodiment of the apparatus according to the invention, said gas bubble generating means comprise an ultrasonic generator with strong negative waves. Suitable ultrasonic generators with strong negative waves are those for which the negative wave can reach a negative value of between several bars and several tens of bars.

According to another advantageous characteristic of the apparatus according to the invention, said apparatus is characterized in that it comprises means for tracking and locating the cells to be destroyed, as well as gas bubbles.

According to yet another advantageous characteristic of the invention, the same generator is used for generating gas bubbles and for imploding said gas bubbles.

In this case, the generator is an ultrasonic type acoustic wave generator.

High power acoustic wave generating apparatus are well known to the practitioner. Any high power acoustic wave generator used for destroying concretions can be used. Such generators include the piezoelectric transducer type acoustic wave generators currently available on the market. It is possible to use the mechanical shockwave generators found on the market, particularly the electrohydraulic type ones which are equipped with focussing means constituted by a truncated ellipsoid, preferably that sold by TECHNOMED under the trade denominations SONOLITH 2000 ® or 3000 ®. The magnetostrictive type generators available on the markets are also suitable, particularly those sold by SIEMENS, or even the mechanical shockwave generators of explosive type, such as described in DE-PS-2 351 247, or detonating type such as described in WO-87/03468, or finally, the laser generators, such as described in DE-A-2 538 260 or EP-A-0 206 332. A work which can also be cited is the book compiled by Lawrence B. Kandler, Med. Doctor, LLOYD H. HARRISON, Med. Doctor, David C. MacCullough, Med. Doctor, in 1987, FUTURA Publishing Company, and entitled "State of the art of extracorporeal Shockwave Lithotripsy", which describes in detail the micro-explosion generators in pages 111 to 145, the authors being Mase Aki KUWAHARA and Kazu Yoshi TAKAYAMA, and the laser generators in pages 97 to 110, the authors being Michael E. Mayo et al.

For the gas bubble generating means, it is possible to inject gas bubble precursor microcapsules having diameters preferably in the 0.5 $\mu$m to 300 $\mu$m range, unrestrictively, which microcapsules encapsulate a gas od selected composition, such as described in document WO-A-80/02365, which gas is injected in the blood stream, either by intraveinous route, or by arterial route at the general level or at the level irrigating the cells to be destroyed. The material encapsulating the gas bubbles is preferably selected to be either gelatin or saccharose. The gas used may be nitrogen or carbon dioxide. Such microbubbles may be produced in accordance with the method described in document WO-A-80/02365 from page 8, line 32 to page 10, line 12 which is incorporated herein by way of reference and which consists in flowing the gas to be encapsulated through a small orifice, for example through a capillary tube, and into a gellable liquid, such as gelatin which has the well known advantage of being non-toxic, non-antigenic and non-allergenic.

Another possibility is to use a solid material precursor of bubbles, which will release gas bubbles when injected into the blood stream, as described in Patent U.S. Pat. No. A-4 265 251, from column 2, line 65, to column 4, the bubbles thus released into the blood stream being readily identifiable by ultrasonic detection means. And it is possible to use particles or microcapsules comprising a hollow inner space, and of which the walls are advantageously formed from a composition containing approximately 80% saccharose and 20% lactose, the hollow space inside the capsules being filled with a gas at a pressure higher than the pressure prevailing in the cardiovascular system. Such capsules or microcapsules encapsulating a gas can be prepared according to the process described in Patent U.S. Pat. No. 3 012 893 and they have the advantage of encapsulating substantially uniform quantities of gas. It is possible, in particular, to use the device described and illustrated with reference to FIG. 3, encapsulating carbon dioxide. The microcapsules obtained according to this process have a diameter in the 0.5 and 350 $\mu$m range and will generate bubbles having a diameter in the 1 and 150 $\mu$m range.

Other materials suitable for producing the walls of the microcapsules encapsulating a gas, are described in EP-A-123 235, in EP-A-131 540 or else in EO-A-0 273 140. Particularly suitable materials for producing the microcapsules walls are lecithin, esters of polyoxyethylene fatty acids, oleates of ricin polyethyleneglycol glycerine, polyoxyethylepolyoxypropylene polymers, esters of saccharose, xyloglycerides, $C_4$–$C_{20}$ non-saturated fatty alcohols, $C_4$–$C_{20}$ non-saturated fatty acids, mono-, di- and tri-triglycerides, esters of fatty acids, constituting in particular between 0.01 and 10% by weight of the injectable solution. Also suitable are cyclodextrine, a monosaccharide, disaccharide or trisaccharide, polyols or mineral or organic salts in a concentration of 5 to 50% by weight, and also maltose, dextrose, lactose or galactose. These compounds may be in aqueous solutions, particularly physiological solutions, such as aqueous 0.9% solutions of NaCl. It is also possible to add compounds to these solutions for increasing the viscosity, for example monopolysaccharides, such as glucose, levulose, galactose, lactose, sorbitol, mannitol, saccharose, dextrane, cyclodextrine, polyols like glycerine or polyglycols. Among substances for increasing viscosity, there are also proteins, or similar substances, aminoacids, blood substitutes such as plasma proteins, gelatine, gelatine derivatives or mixtures thereof. Concentration may vary between 0.5 and 50% by weight, the highest concentration being limited by the capacity to dissolve of the substance. Surfactants, which also have a viscosity increasing effect, such as for example the poloxyethylene polymers whose molecular weight may range between about 4,500 and 16,500 in a proportion of 1% to 20%, and preferably about 3% to 10%, can also be added in the solution.

Such microcapsules are easily identifiable by ultrasonic type tracking and locating means working at a frequency which may vary between several hundreds MHz and about ten MHz.

The gas bubbles can also be created in situ by a phenomenon of cavitation provoked by an ultrasonic wave generator working in a frequency range of about $10^4$ to $10^5$ Hz, said ultrasonic waves thus lasting between about a fraction of a second and a few seconds depending on the power of the wave which is necessary to the formation of nucleies and to the growth of bubbles in situ in the biological fluids surrounding the cells to be destroyed, in particular in the blood of the vessels, including the capillaries, surrounding the cells to be destroyed.

BRIEF DESCRIPTION OF THE DRAWING

The invention will be more readily understood on reading the following description with reference to the accompanying drawing in which the one and only figure represents diagrammatically and non-restrictively a partial cross-section of a currently preferred embodiment of the apparatus for selective destruction of cells inside a living subject's body, according to the invention.

DETAILED DESCRIPTION OF PREFERRED EMBODIMENT

Referring to the one Figure, this shows a currently preferred apparatus according to the invention, designated by the general reference 10, for selective destruction of cells symbolically designated by the general reference 12, and situated inside a living subject's body 14, in particular a mammal, a human being in this case, lying for example on a support table 16 comprising an opening 18 to allow the treatment of selective destruction of the cells 12.

The apparatus 10 according to the invention is characterized in that it comprises:

a) means, designated by the general reference number 20, for generating, in situ, gas bubbles 22 within the cells 12 to be selectively destroyed; and b) implosion means, designated by the general reference number 24, capable of provoking, in situ, an implosion of the gas bubbles 22, which will result in the destruction of cells 12 to be destroyed situated adjacent the imploded gas bubbles 22.

Said implosion means 24 for imploding the gas bubbles 22 are advantageously constituted by high power acoustic wave generating means, which preferably generate pressure waves ranging between several tens and several hundreds bars. This pressure compresses the gas bubbles until they disintegrate.

According to one particular embodiment, the implosion means 24 comprise an acoustic generator of piezoelectric type, preferably comprising focussing means capable of focussing in a target-focus F, comprising for example a hemispherical-type focussing surface 28, as known of anyone skilled in the art. Such piezoelectric transducer-type focussing acoustic generators are available on the market, particularly for destroying concretions, such as kidney lithiases or cholelithiases.

According to another particular embodiment of the invention, the implosion means 24 comprise a mechanical shockwave generator. The mechanical shockwaves can be generated by an electrohydraulic-type generator, preferably provided with focussing means 26 comprising a truncated ellipsoid. Such apparatus is well known of anyone skilled in the art and available on the market. Advantageous examples of such apparatus are the TECHNOMED apparatus sold under the trade denomination SONOLITH 2000 ® or 3000 ® and used up to now for destroying concretions and in particular kidney lithiases or cholelithiases.

Magnetostrictive-type shockwave generators, equally well known of anyone skilled in the art, may also be used, and particularly the apparatus sold by the company SIEMENS.

Laser mechanical shockwave generators, also well known of anyone skilled in the art also suitable.

And finally, the explosive-type mechanical shockwave generators, comprising for example the explosion of an exploding wire as conventionally known to anyone skilled in the art, may also be used.

The means 20 for generating gas bubbles 22 according to the invention are described in detail in the introductory part of the present description. It can, for example, be an injectable solution contained in a container 20 and which is injected into the blood stream, either by intraveinous route, or through the arteries 30, at the general level or at the level irrigating the tissues 12 to be destroyed, as this is clearly illustrated and easy to understand for anyone skilled in the art from the accompanying drawing. The gas bubbles may be bubbles of nitrogen carbon dioxide or an inert gas bubbles, such as used in diving cylinders, for example helium.

According to another advantageous characteristic of the apparatus according to the invention, said apparatus further comprises means 32 for tracking and locating the cells 12 to be destroyed. Said tracking means 32 can advantageously be constituted by an auxiliary ultrasonic probe 32, connected for example via a conductor 36 to an image-forming device 38 capable of forming an image on a screen 40.

A central control device 42 may also be provided for collecting information received from device 38 and for controlling the implosion means 24 as a function of the received information. In general, the high power acoustic wave generating apparatus already available on the market are all equipped with auxiliary tracking and locating means 32 and with control means 42 permetting a correlation between the location and positioning of the target to be destroyed 12 in focus point F of the acoustic waves generating means 24–26 focussed at said focal point F.

In general, the destruction of cells 12 to be destroyed, such as tumors, i.e. cells of soft tissues, or nervous links, is obtained with a treatment using acoustic waves generated by implosion means 24–26, and having a pressure value of +300 bars for the positive wave and of −100 bars for the negative wave.

By way of example, complete destruction of a tumor in a rabbit's liver is achieved in vivo by applying 300 to 500 elementary waves, one wave having a rise time of approximately 100 ns and a fall time of 1 μs.

The organ to be treated, in this case the liver, is first located by any conventional tracking and locating means, such as for example an ultrasonic probe 34, X- rays, NMR or any other detection means available to anyone skilled in the art. A system is advantageously provided for bringing the locating means 32 in coincidence with the implosion means 24, as well known of anyone skilled in the art and as recalled in the foregoing description.

It is worth noting that the gas bubbles 22 which are introduced in situ by any one of the precedingly described means, will be easily viewed by any ultrasonic means since they increase the contrast by said locating means.

It is thus found that, with the apparatus according to the invention, new therapeutic treatments can be conducted in a simple extracorporeal way, the technique used permitting the destruction of very small tumors immediately the waves are focussed in a volume equal to the volume to be destroyed. For example a volume as little as 1 mm 3 can be destroyed with ultrasonic-type waves, and tumors of volume as reduced as 1 cm 3 with mechanical shock waves, generated in particular by electrohydraulic means.

Consequently, the apparatus according to the invention also permits the treatment of metastases.

With the apparatus according to the invention, all such therapeutic treatments can be applied in a versatile manner due to the fact that the implosion means 24 can be provided by a large number of various apparatus, all of which offer their own particular advantages which may be particularly suited for one particular treatment.

Also, as described hereinabove, the gas bubbles can be brought in situ by many different ways. And also the diameter of these gas bubbles can vary within wide limits. A maximum limit is when the diameter of the bubbles is so large that there is a risk of embolism for adjacent organs, whereas when the bubbles are too small they run the risk of being eliminated before the treatment is started. It is therefore preferred to use very stable gas bubbles such as those previously described, whose diameter can vary between 0.1 and about 300 µm.

It is finally found that the game generator can be used for creating the gas bubbles in situ, due to cavitation phenomena, and for destroying the cells 12 to be destroyed in focus point F. In the first case, the generator will work at low power to pass, in a second stage, to the emission of high power waves capable of imploding the gas bubbles created by the cavitation phenomena caused by the low power waves. This will be particularly easy with ultrasonic type generators using piezoelectric elements. When these apparatus are worked at several tens of KHz, gas bubbles are created in situ because of the cavitation phenomena, whereas when they are worked at between several hundreds KHz and several MHz, the gas bubbles will implode and the surrounding cells 12 situated in the focus point F will be destroyed.

The invention also relates to a therapeutic treatment method for selective destruction of cells inside a living subject's body, in particular a mammal, including a human being, characterized in that it consists in generating gas bubbles in situ within the cells to be selectively destroyed and in imploding said gas bubbles, the implosion causing a destruction of the cells to be destroyed situated near the imploded gas bubbles.

Special embodiments of this method are clear to anyone skilled in the art reading the foregoing description.

The present invention also relates to a method for treating metastases, characterized in that it consists in generating gas bubbles within or in the immediate vicinity of metastases, and in provoking the implosion of said gas bubbles, thereby causing the destruction of the metastases.

Obviously the invention is not limited to the above described embodiments and on the contrary covers all technical means which are technical equivalents of the means described herein, as well as their various combinations.

What is claimed is:

1. An apparatus for selective destruction of cells inside a living subject's body, wherein said apparatus comprises:
   means for generating gas bubbles in situ in proximity to the cells to be selectively destroyed, and
   means for provoking an implosion in situ of the gas bubbles, thereby destroying the cells adjacent the imploded gas bubbles.

2. Apparatus as claimed in claim 1, wherein said means for provoking an implosion comprise means for generating high power acoustic waves.

3. Apparatus as claimed in claim 2, wherein said high power acoustic waves have a pressure of at least 30 bars.

4. The apparatus of claim 3, wherein said high power acoustic waves have a pressure of at least 100 bars.

5. The apparatus of claim 3, wherein said high power acoustic waves have a pressure of at least 300 bars.

6. Apparatus as claimed in claim 2, wherein said acoustic wave generating means comprise a piezoelectric transducer type acoustic generator.

7. Apparatus as claimed in claim 2, wherein said acoustic wave generating means comprise a mechanical shock wave generator selected from the group consisting of electrohydraulic, magnetostrictive, laser and explosive type.

8. Apparatus as claimed in claim 2, wherein said apparatus further comprises central control means for controlling said means for provoking the implosion.

9. Apparatus as claimed in claim 1, wherein said means for generating gas bubbles comprise means for feeding a precursor in which to generate the gas bubbles in situ.

10. Apparatus as claimed in claim 9, wherein said precursor feeding means comprise a reservoir of an injectable solution containing said generated gas bubbles.

11. Apparatus as claimed in claim 1, wherein said means for generating gas bubbles comprise a material which is a precursor of gas bubbles.

12. Apparatus as claimed in claim 11, wherein said gas bubble precursor material comprises capsules or microcapsules encapsulating the gas bubbles, the walls of said capsules or microcapsules being produced from a material which dissolves progressively in the blood stream.

13. Apparatus as claimed in claim 12, wherein the wall of said capsules or microcapsules is made of a compound selected from the group consisting of gelatin, lecithin, esters of polyoxyethylene fatty acids, oleate of polyethyleneglycol glycerin ricin, polyoxyethylenpolyoxypropylene polymers, an ester of saccharose, a $C_4$–$C_{20}$ non-saturated fatty alcohol, a $C_4$–$C_{20}$ non-saturated fatty acid, a monoglyceride, diglyceride, triglyceride, maltose, dextrose, lactose and galactose.

14. Apparatus as claimed in claim 1, wherein said means for generating gas bubbles comprise cavitation means generating gas bubbles in situ by cavitation phenomena.

15. Apparatus as claimed in claim 14, wherein said cavitation means comprise an ultrasonic generator with high negative waves having pressures in a range from about three bars to about 100 bars.

16. Apparatus as claimed in claim 1, further comprising means for tracking and locating the cells to be destroyed and the gas bubbles, said tracking and locating means comprising an ultrasonic probe.

17. Apparatus as claimed in claim 1, further comprising means for tracking and locating the cells to be destroyed and the gas bubbles.

18. The apparatus according to claim 1, wherein said means for generating gas bubbles comprises means for generating gas bubbles having a diameter ranging from 0.5 to 350 microns.

19. A method for extracorporeal selective destruction of cells in a living subject, comprising the steps of:
generating gas bubbles in proximity to said cells;
generating pressure waves; and
focussing said pressure waves on said bubbles for imploding said bubbles thereby destroying said cells.

20. The method of claim 19, wherein said step of generating gas bubbles includes injecting a precursor of gas bubbles into the blood stream of said subject so as to generate said gas bubbles in situ.

21. The method of claim 20, wherein said precursor includes microcapsules encapsulating said gas bubbles, said microcapsules having walls made of a material which progressively dissolves in the blood stream.

22. The method of claim 21, wherein said material is selected from the group consisting of gelatin, lecithin, esters of polyoxyethylene fatty acids, oleate of polyethyleneglycol glycerin, ricin, polyoxyethylenpolyoxypropylene polymers, an ester of saccharose, a $C_4$–$C_{20}$ non-saturated fatty alcohol, a $C_4$–$C_{20}$ non-saturated fatty acid, a monoglyceride, diglyceride, triglyceride, maltose, dextrose, lactose and galactose.

23. The method of claim 22, wherein said step of generating said pressure waves comprises a step of generating high power acoustic waves.

24. The method of claim 23, wherein said acoustic waves have a pressure of at least 30 bars.

25. The method of claim 21, wherein said step of generating said pressure waves comprises a step of generating high power acoustic waves.

26. The method of claim 25, wherein said acoustic waves have a pressure of at least 30 bars.

27. The method of claim 20, wherein said step of generating pressure waves comprises a step of generating high power acoustic waves.

28. The method of claim 27, wherein said acoustic waves have a pressure of at least 30 bars.

29. The method of claim 19, wherein said step of generating gas bubbles includes injecting a solution into the blood stream of said subject, said solution containing a precursor in which to generate said bubbles in situ.

30. The method of claim 29, wherein said step of generating said pressure waves comprises a step of generating high power acoustic waves.

31. The method of claim 30, wherein said acoustic waves have a pressure of at least 30 bars.

32. The method of claim 19, wherein said step of generating gas bubbles includes forming said bubbles in situ within said cells by a cavitation means.

33. The method of claim 32, wherein said cavitation means comprise an ultrasonic generator.

34. The method of claim 33, wherein said step of generating said bubbles comprises forming said bubbles by negative ultrasonic waves having negative pressures sufficient to create said bubbles by cavitation.

35. The method of claim 34, wherein said negative pressures are in a range from about 3 bars to about 100 bars.

36. The method of claim 33, wherein said step of generating pressure waves comprises a step of generating high power acoustic waves.

37. The method of claim 36, wherein said acoustic waves have a pressure of at least 30 bars.

38. The method of claim 32, wherein said step of generating said pressure waves comprises a step of generating high power acoustic waves.

39. The method of claim 38, wherein said acoustic waves have a pressure of at least 30 bars.

40. The method of claim 19, wherein said step of generating said pressure waves comprises a step of generating high power acoustic waves.

41. The method of claim 40, wherein said acoustic waves have a pressure of at least 30 bars.

42. The method of claim 41, wherein said acoustic waves have a pressure of at least 100 bars.

43. The method of claim 42, wherein said acoustic waves have a pressure of at least 300 bars.

44. The method of claim 40, wherein said step of generating high power acoustic waves uses a piezoelectric transducer type acoustic generator.

45. The method of claim 40, wherein said means for generating high power acoustic waves comprise a mechanical shock wave generator selected from the group consisting of electrohydraulic, magnetostrictive, laser and explosive type generators.

46. The method of claim 19, wherein said step of generating said bubbles in situ includes providing means for feeding a precursor in which to generate said gas bubbles in situ.

47. The method of claim 19, further comprising a step of tracking and locating the cells to be destroyed and the gas bubbles.

48. The method of claim 47, wherein said step of tracking and locating includes providing an ultrasonic probe.

49. The method according to claim 19, wherein said gas bubble generating step comprises generating gas bubbles having a diameter ranging from 0.5 to 350 microns.

* * * * *